United States Patent [19]

Grassme

[11] Patent Number: 4,501,010
[45] Date of Patent: Feb. 19, 1985

[54] DENTAL X-RAY DIAGNOSTIC INSTALLATION

[75] Inventor: Ulrich Grassme, Nuremberg, Fed. Rep. of Germany

[73] Assignee: Siemens Aktiengesellschaft, Berlin & Munich, Fed. Rep. of Germany

[21] Appl. No.: 425,445

[22] Filed: Sep. 28, 1982

[30] Foreign Application Priority Data

Oct. 30, 1981 [DE] Fed. Rep. of Germany ....... 3143157

[51] Int. Cl.³ .............................................. G03B 41/16
[52] U.S. Cl. ...................................... 378/38; 378/91; 378/108
[58] Field of Search ....................... 378/38, 39, 40, 91, 378/108

[56] References Cited

U.S. PATENT DOCUMENTS

| | | |
|---|---|---|
| 4,021,672 | 5/1977 | Franke . |
| 4,063,099 | 12/1977 | Grassme ................................ 378/39 |
| 4,286,162 | 8/1981 | Suzuki ................................. 378/40 |
| 4,333,012 | 6/1982 | Furuichi .............................. 378/38 |

Primary Examiner—Craig E. Church
Attorney, Agent, or Firm—Hill, Van Santen, Steadman & Simpson

[57] ABSTRACT

An exemplary embodiment comprises an exposure unit including an X-ray tube and a cassette holder rotatable about vertical axes and between which the head of the patient is disposed. A radiation detector is disposed at the cassette holder for supplying an electrical signal corresponding to the dose rate when it is struck by X-rays and being interconnected with an X-ray tube voltage controller and a dose rate regulator in such manner that the X-ray tube voltage is influenced by the output of the radiation detector to control the dose rate to a value producing an optimum film blackening. A function generator determining the speed of the exposure unit is provided in which a speed curve is stored given which the radiation dose influencing the film is approximately constant.

1 Claim, 2 Drawing Figures

DENTAL X-RAY DIAGNOSTIC INSTALLATION

BACKGROUND OF THE INVENTION

The invention relates to a dental X-ray diagnostic installation comprising an exposure unit rotatable around vertical axes and including an X-ray tube and cassette holder, and comprising a head support lying between the X-ray tube and cassette holder, for producing general or overall exposures, in which a radiation detector is attached to the cassette holder, the radiation detector supplying an electrical signal corresponding to the dose rate when it is struck by X-rays and which is interconnected to setting means and a dose rate regulator to form an automatic exposure unit, being inter-connected in such manner that the X-ray tube voltage is influenced by the output signal of the radiation detector for the purpose of controlling the dose rate to a value producing an optimum film blackening.

An X-ray diagnostic installation of this type is disclosed in U.S. Pat. No. 4,021,672 issued May 3, 1977. Given this X-ray diagnostic installation, the setting of the exposure values, particularly of the X-ray tube voltage and/or of the X-ray tube current are accordingly adapted to the density (transmissivity) conditions of the patient in such manner that the mean radiation dose influencing the individual film sections is maintained constant. The density can fluctuate relatively greatly within the examined area of the patient. Relatively great differences of density also particularly derive between individual patients, for example between children and adults. Accordingly, a relatively large range of adjustment results when the radiation dose is held constant only by controlling the described exposure parameters.

SUMMARY OF THE INVENTION

The object of the invention is to create an X-ray diagnostic installation of the type initially described in which, given employment of the X-ray tube voltage as the manipulated variable for controlling the dose rate, the range within which the X-ray tube voltage is adjusted is kept relatively small. What is thereby meant to be achieved is that the X-ray tube voltage determining the image contrast deviates only relatively slightly on the basis of the regulation from the optimum value for the respective patient.

This object is inventively achieved in that a function generator determing the speed of the exposed unit is provided, in which function generator a speed curve can be stored given which the radiation dose influencing the film is approximately constant. Given the inventive X-ray diagnostic installation, holding the radiation dose influencing the respective film section roughly constant ensues in that the function generator prescribes the cycle speed of the exposure unit in accord with the density conditions in the patient. It is only the fine control which ensues over the X-ray tube voltage.

In the following, the invention is described in greater detail on the basis of an exemplary embodiment illustrated on the accompanying drawing sheet; and other objects, features and advantages will be apparent from this detailed disclosure and from the appended claims.

DETAILED DESCRIPTION

Figure 1:
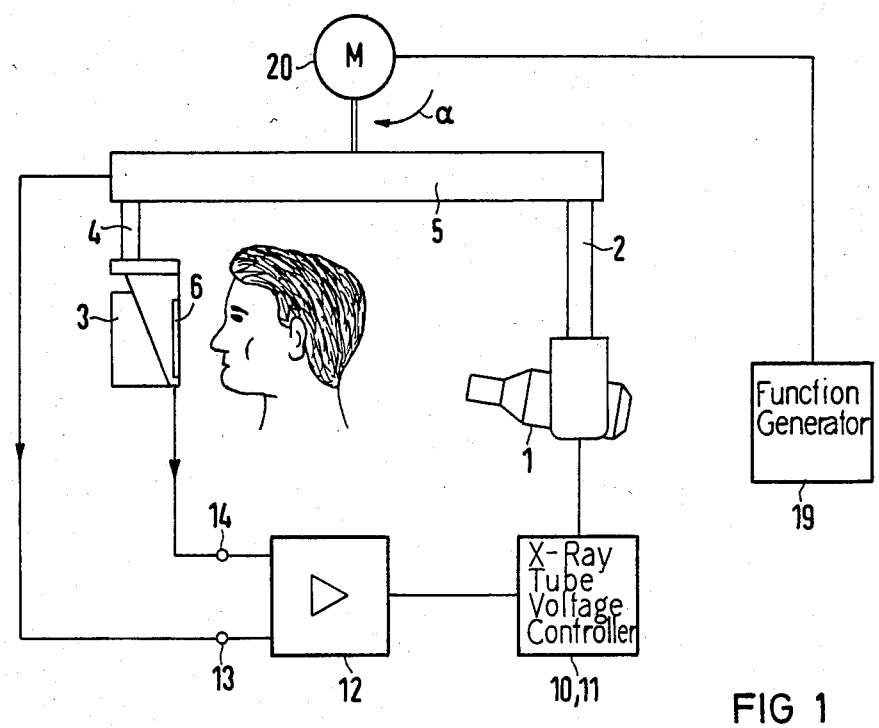
FIG. 1 shows the fundamental structure of an X-ray diagnostic installation according to the invention.

The X-ray diagnostic installation illustrated in FIG. 1 contains an X-ray tube in a housing 1, said X-ray tube being height-adjustably mounted by a carrier 2. The X-ray film is secured in a semicircularly bent cassette at a cassette holder 3. The cassette holder 3 is secured to a carrier 4. The carriers 2 and 4 are connected to a holding device 5. A head support lies between the cassette holder 3 and the X-ray tube housing 1. As viewed in the beam direction, a slit diaphragm 6 is disposed in front of the cassette holder 3.

In order to produce a general or overall tooth or jaw layer exposure, the head of the patient is supported within the exposure unit. During an exposure, the X-ray tube housing 1 together with the X-ray tube and the cassette holder 3, with the film attached thereto, move around the head of the patient. To that end, a motor 20 in the holding device 5 drives said device 5 with the carriers 2 and 4. Thereby, both the X-ray housing 1 and the cassette holder 3 are rotated around vertical axes in such manner that the X-rays always strike the teeth at a right angle and a constant-spacing row of teeth/film always exists. During the movement of the cassette holder 3 and the X-ray housing 1 around the head of the patient, the jaw and, successively, the teeth are imaged on the film. The cassette with the X-ray film is moved past behind the slit diaphragm 6 with a rigidly prescribed speed rate (or: curve).

Figure 2:
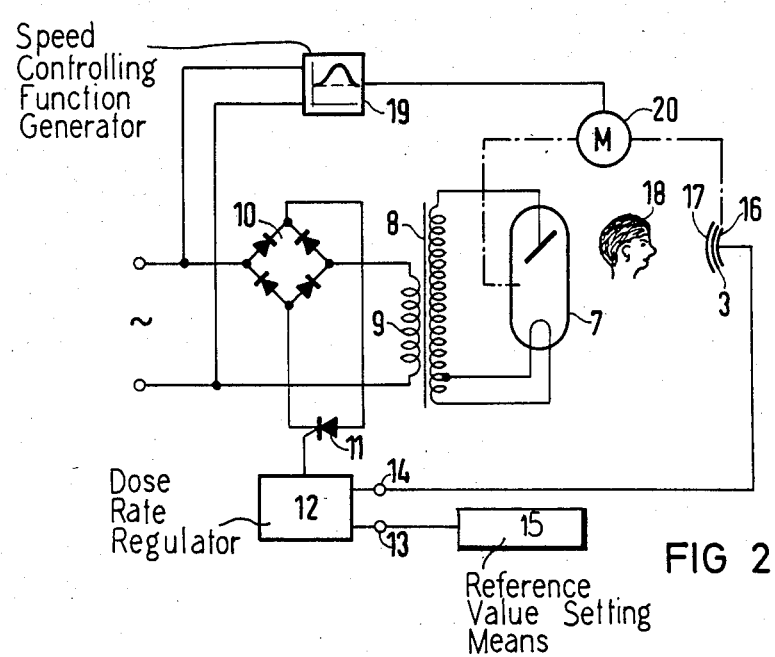
FIG. 2 shows a circuit diagram of an inventive X-ray diagnostic installation.

The X-ray tube 7 in the housing 1 is diagrammatically illustrated in FIG. 2, said X-ray tube 7 being supplied with high voltage by the secondary winding of a high voltage transformer 8, and also with filament voltage. The primary winding 9 of the high voltage transformer 8 can be connected via a diode bridge 10 to an a.c. supply, a thyristor 11 lying in the DC branch of bridge 10. The thyristor 11 forms a kV regulator and receives trigger pulses from a dose rate regulator 12 which has a reference value input 13 and an actual value input 14. The reference value signal is supplied by a reference value setting means 15 which is set according to the respective film speed, whereas the actual value signal for the dose rate is supplied by a radiation detector 16 which lies behind the X-ray film 17 secured to the cassette holder 3. The head 18 of the patient lies between the X-ray tube 7 and the X-ray film 17. The cassette containing the X-ray film is not illustrated.

At its input 13, the dose rate regulator 12 receives a signal which produces an optimum film blackening for the particular X-ray film 17. As a function of the difference between this signal and the actual value signal at the input 14, the regulator 12 sets the operation of the trigger pulses supplied to the thyristor 11 in such manner that the dose rate is held constant.

In the illustrated exemplary embodiment, the X-ray tube voltage is varied according to the ignition timing of the thyristor 11 for the control of the dose rate. The dose rate regulator 12 can contain a differential amplifier for measuring the difference between the signals at the inputs 13 and 14.

A function generator 19 which prescribes the speed for the motor 20 is provided for the purpose of contracting the range of adjustment and, thus, the setting range over which the X-ray tube voltage is varied. The respectively optimum velocity curve at which the radiation dose influencing the individual locations of the X-ray film 17 is approximately constant is stored in the function generator 19 for the various patient constitutions. Accordingly, the X-ray tube voltage is only varied by the dose rate regulator 12 within a relatively small range and, accordingly, deviates only slightly from a value which is favorable in terms of exposure technology.

It will be apparent that many modifications and variations may be made without departing from the scope of the teachings and concepts of the present invention.

I claim as my invention:

1. A dental X-ray diagnostic installation comprising an exposure unit including an X-ray tube and a cassette holder, movable about a head location lying between the X-ray tube and the cassette holder for producing general exposures, a radiation detector which supplies an electrical output signal corresponding to the dose rate when it is struck by X-radiation being attached to the cassette holder, automatic exposure control means coupled with said radiation detector and including a dose rate regulator and an X-ray tube voltage control means interconnected in such manner that the X-ray tube voltage is influenced by the output signal of the radiation detector for the purpose of the control of the dose rate to a value producing an optimum film blackening, a single motor coupled with said X-ray tube and with said cassette holder for effecting movement thereof about the head location for the production of a general exposure during an exposure operation, and a function generator coupled with said single motor, said function generator storing respectively optimum velocity curves for various patient constitutions and controlling the speed of the single motor during an exposure operation for a given patient constitution such that the radiation dose influencing successive locations of an X-ray film in the cassette holder is approximately constant for the given patient constitution, and such that the dose rate regulator is only required to vary the radiation output from the X-ray tube within a relatively small range in comparison to the range which would be required in the absence of control of the speed of said single motor by said function generator.

* * * * *